United States Patent
Camacho et al.

(10) Patent No.: US 6,934,576 B2
(45) Date of Patent: Aug. 23, 2005

(54) DETERMINATION OF THE ULTRASTRUCTURE OF CONNECTIVE TISSUE BY AN INFRARED FIBER-OPTIC SPECTROSCOPIC PROBE

(75) Inventors: Nancy P. Camacho, Edison, NJ (US); Mathias P. B. Bostrom, Scarsdale, NJ (US); Paul West, Brooklyn, NY (US)

(73) Assignee: Hospital for Special Surgery, New York, NY (US)

( * ) Notice: Subject to any disclaimer, the term of this patent is extended or adjusted under 35 U.S.C. 154(b) by 588 days.

(21) Appl. No.: 09/853,298

(22) Filed: May 10, 2001

(65) Prior Publication Data

US 2002/0010400 A1 Jan. 24, 2002

Related U.S. Application Data

(60) Provisional application No. 60/204,194, filed on May 12, 2000.

(51) Int. Cl.[7] ................................................. A61B 6/00
(52) U.S. Cl. .................... 600/473; 600/475; 436/63; 436/164; 436/171; 250/341.2
(58) Field of Search ................................ 600/473, 475; 436/63, 169, 171, 172, 164; 250/341.2

(56) References Cited

U.S. PATENT DOCUMENTS

| 3,769,963 A | 11/1973 | Goldman et al. |
| 4,336,809 A | 6/1982 | Clark |
| 4,588,885 A | 5/1986 | Lovoi et al. |

(Continued)

FOREIGN PATENT DOCUMENTS

DE 19841217 A1 4/1999

OTHER PUBLICATIONS

US 6,230,044, 5/2001, Afanassieva et al. (withdrawn)

*Infrared and Raman Spectroscopy of Biological Materials*, Eds. Gremlich, H.U., Yan, B., New York, Marcel–Dekker, pp. 323–377 (2001).

Camacho, N.P., Hou, L., Toledano, T.R., Ilg, W.A., Brayton, C.F., Raggio, C.L., Root, L., and Boskey, A.L., "The Material Basis for Reduced Mechanical Properties in Oim Mice Bones", *J. Bone Miner. Res.*, 14, pp. 264–272, (1999).

Lazarev, Y.A., Grishkovsky, B.A., and Khromova, T.B., "Amide I Band of IR Spectrum and Structure of Collagen and Related Polypeptides", *Biopolymers*, 24, pp. 1449–1478, (1985).

(Continued)

*Primary Examiner*—Ruth S. Smith
(74) *Attorney, Agent, or Firm*—Frishauf, Holtz, Goodman & Chick, P.C.

(57) ABSTRACT

A method for the evaluation of the ultrastructure of connective tissue, such as cartilage, including (a) providing a probe operative in the near-infrared or mid-infrared region of the electromagnetic spectrum, (b) positioning the probe either to be in contact with the connective tissue (for detecting attenuated total reflectance) or within a sufficient distance from the surface of the connective tissue (for detecting reflection), (c) detecting infrared radiation which penetrates the surface of the connective tissue for detecting attenuated total reflectance or which reflects off the surface of the connective tissue and (d) analyzing the infrared radiation from step (c) for at least one of peak height, peak area and frequency, and comparing at least one of the peak height, the peak area and the frequency for established values for at least one of peak height, peak area and frequency for normal connective tissue to detect a modification in the molecular structure of the connective tissue.

20 Claims, 11 Drawing Sheets

U.S. PATENT DOCUMENTS

| | | | |
|---|---|---|---|
| 4,733,660 A | 3/1988 | Itzkan |
| 4,737,628 A | 4/1988 | Lovoi |
| 4,973,848 A | 11/1990 | Kolobanov et al. |
| 5,038,039 A | 8/1991 | Wong et al. |
| 5,170,056 A | 12/1992 | Berard et al. |
| 5,197,470 A | 3/1993 | Helfer et al. |
| 5,204,517 A | 4/1993 | Cates et al. |
| 5,280,788 A | 1/1994 | Janes et al. |
| 5,281,798 A | 1/1994 | Hamm et al. |
| 5,286,947 A | 2/1994 | Clyde et al. |
| 5,304,173 A | 4/1994 | Kittrell et al. |
| 5,346,488 A | 9/1994 | Prince et al. |
| 5,452,716 A | 9/1995 | Clift |
| 5,460,182 A | 10/1995 | Goodman et al. |
| 5,516,043 A | 5/1996 | Manna et al. |
| 5,527,273 A | 6/1996 | Manna et al. |
| 5,701,913 A | 12/1997 | McPherson et al. |
| 5,733,739 A | 3/1998 | Zakim et al. |
| 5,746,736 A | 5/1998 | Tankovich |
| 5,762,609 A | 6/1998 | Benaron et al. |
| 5,769,791 A | 6/1998 | Benaron et al. |
| 5,772,597 A | 6/1998 | Goldberger et al. |
| 5,785,658 A | 7/1998 | Benaron et al. |
| 5,807,261 A | 9/1998 | Benaron et al. |
| RE36,044 E | 1/1999 | Benaron |
| 5,876,397 A | 3/1999 | Edelman et al. |
| 5,923,808 A | 7/1999 | Melling |
| 5,986,770 A | 11/1999 | Hein et al. |
| 5,987,346 A | 11/1999 | Benaron et al. |
| 6,036,667 A | 3/2000 | Manna et al. |
| 6,063,050 A | 5/2000 | Manna et al. |
| 6,068,604 A | 5/2000 | Krause et al. |
| 6,135,774 A | 10/2000 | Hack et al. |
| 6,200,307 B1 | 3/2001 | Kasinkas et al. |
| 6,270,471 B1 | 8/2001 | Hechl et al. |
| 6,324,419 B1 | 11/2001 | Guzelsu et al. |
| 2001/0048077 A1 | 12/2001 | Afanassieva |
| 2002/0169379 A1 | 11/2002 | Camacho et al. |

OTHER PUBLICATIONS

Liu, K.Z., Dembinski, T.C., and Mantsch, H.H., "Rapid Determination of Fetal Lung Maturity from Infrared Spectra of Amniotic Fluid", *Am. J. Obstet. Gynecol.*, 178, pp. 234–241, (1998).

Mendelsohn, R., and Moore, D.J., "Vibrational Spectroscopic Studies of Lipid Domains in Biomembranes and Model Systems", *Chem. Phys. Lipids*, 96, pp. 141–157, (1998).

Moore, D.J., Rerek, M.E., and Mendelsohn, R., "Lipid Domains and Orthorhombic Phases in Model Stratum Corneum: Evidence from Fourier Transform Infrared Spectroscopy Studies", *Biochem. Biophys. Res. Commun.*, 231, pp. 797–801, (1997).

Moore, D.J., Gioioso, S., Sills, R.H., and Mendelsohn, R., "Some Relationships Between Membrane Phospholipid Domains, Conformational Order, and Cell Shape in Intact Human Erythrocytes", *Biochim. Biophys. Acta.*, 1415, pp. 342–348, (1999).

Paschalis, E.P., Betts, F., DiCarlo, E., Mendelsohn, R., and Boskey, A.L., "FTIR Microspectroscopic Analysis of Normal Human Cortical and Trabecular Bone", *Calcif. Tissue Int.*, 61, pp. 480–486, (1997).

Paschalis, E.P., Betts, F., DiCarlo, E., Mendelsohn, R., and Boskey, A.L., "FTIR Microspectroscopic Analysis of Human Iliac Crest Biopsies from Untreated Osteoporotic Bone", *Calcif. Tissue Int.*, 61, pp. 487–492, (1997).

Camacho, N.P., Landis, W.J., and Boskey, A.L., "Mineral Changes in a Mouse Model of Osteogenesis Imperfecta Detected by Fourier Transform Infrared Microscopy", *Connect. Tissue Res.*, 35, pp. 259–265, (1996).

Camacho, N.P., Rimnac, C.M., Meyer, R.A.J., Doty, S., and Boskey, A.L., "Effect of Abnormal Mineralization on the Mechanical Behavior of X–Linked Hypophosphatemic Mice Femora", *Bone*, 17, pp. 271–278, (1995).

Gadaleta, S.J., Camacho, N.P., Mendelsohn, R., and Boskey, A.L., "Fourier Transform Infrared Microscopy of Calcified Turkey Leg Tendon", *Calcif. Tissue Int.*, 58, pp. 17–23, (1996).

Boskey, A.L., Guidon, P., Doty, S.B., Stiner, D., Leboy, P., and Binderman, I., "The Mechanism of Beta–Glycerophosphate Action in Mineralizing Chick Limb–Bud Mesenchymal Cell Cultures", *J. Bone Miner. Res.*, 11, pp. 1694–1702, (1996).

Kidder, L.H., Kalasinsky, V.F., Luke, J.L., Levin, I.W., and Lewis, E.N., "Visualization of Silicone Gel in Human Breast Tissue Using New Infrared Imaging Spectroscopy", *Nat. Med.*, 3, pp. 235–237, (1997).

Lewis, E.N., Kidder, L.H., Levin, I.W., Kalasinsky, V.F., Hanig, J.P., and Lester, D.S., "Applications of Fourier Transform Infrared Imaging Microscopy in Neurotoxicity", *Ann. N.Y. Acad., Sci.*, 820, pp. 234–247, (1997).

Marcott, C., Reeder, R.C., Paschalis, E.P., Tatakis, D.N., Boskey, A.L., and Mendelsohn, R., "Infrared Microspectroscopic Imaging of Biomineralized Tissues Using a Mercury–Cadmium–Telluride Focal–Plane Array Detector", *Cell. Mol. Biol. (Noisy–le–grand)*; 44, pp. 109–115, (1998).

Camacho, N.P., Mendelsohn, R., Grigiene, R., Torzilli., P.A., "Polarized FI–IR Microscopic Determination of Collagen Orientation in Articular Cartilage", 42nd Annual Meeting, Orthopaedic Research Society, Feb. 19–22, 1996, Atlanta, Georgia.

Camacho, N.P., West, P., Torzilli, P.A., Mendelsohn, R., "FTIR Microscopic Imaging of Collagen and Proteoglycan in Bovine Cartilage", *Biopolymers*, 62:1–8 (2001).

Potter, K., Kidder, L.H., Levin, I.W., Lewis E.N., Spencer R.G., "Imaging of Collagen and Proteoglycan in Cartilage Sections Using Fourier Transform Infrared Spectral Imaging", *Arthritis & Rheum* 44(4) :846–855 (2001).

Schumacher, H.R., Klippel, J.H., and Koopman, W.J., "Articular Cartilage", *Primer on the Rheumatic Diseases*, 11th edition, Atlanta: The Arthritis Foundation, pp. 14–18, (1993).

Horecker, B., Kaplan, N.O., Marmur, J., and Scheraga, H.A., "Collagens", *Conformation in Fibrous Proteins and Related Synthetic Polypeptides*, New York: Academic Press, editors Fraser, R.D.B. and MacRae, T.P., pp. 344–402, (1973).

George, A., and Veis, A., "FTIRS in $H_2O$ Demonstrates that Collagen Monomers Undergo a Conformational Transition Prior to Thermal Self–Assembly In Vitro", *Biochemistry*, 30, pp. 2372–2377, (1991).

Lazarev, Y.A., Grishkovsky, B.A., Khromova, T.B., Lazareva, A.V., and Grechishko, V.S., "Bound Water in Collagen– Like Triple Helical Structure", *Biopolymers*, 32, pp. 189–195, (1992).

Bychkov, S.M., and Kuzmina, S.A., "Study of Tissue Proteoglycans by Means of Infrared Spectroscopy", *Biull. Eksp. Biol. Med.*, 114, pp. 246–249, (1992).

Bychkov, S.M., Bogatov, V.N., and Kuzmina, S.A., "Infrared Spectra of Cartilage Proteoglycans", *Bull. Eksp. Biol. Med.*, 90, pp. 561–563, (1980).

Bychkov, S.M., Bogatov, V.N., and Kuzmina, S.A., "Study of Different Proteoglycan Salts", *Bull. Eksp. Biol. Med.*, 92, pp. 302–305, (1981).

Buckwalter, J.A., and Mow, V.C., "Injuries to Cartilage and Meniscus: Sports Injuries to Articular Cartilage", DeLee, J.C., and Drez, D., Jr., *Orthopaedic–Sports Medicine Principles and Practice*, Philadelphia: W.B. Saunders Company, pp. 82–107, (1994).

Potter, H.G., Linklater, J.M., Allen, A.A., Hannafin, J.A., and Haas, S.B., "Magnetic Resonance Imaging of Articular Cartilage in the Knee: An Evaluation with Use of Fast–Spin–Echo Imaging", *J. Bone Joint, Surg. Am.*, 80, pp. 1276–1284, (1998).

Recht, M.P., and Resnick, D., "Magnetic Resonance Imaging of Articular Cartilage: An Overview" *Top. Magn. Reson. Imaging*, 9, pp. 328–336, (1998).

Speer, D.P., and Dahners, L., "The Collagenous Architecture of Articular Cartilage, Correlation of Scanning Electron Microscopy and Polarized Light Microscopy Observations", *Clin. Orthop.*, 167, pp. 267–275, (1979).

Panula, H.E., Hyttinen, M.M., Arokoski, J.P., Langsjo, T.K., Pelettari, A., Kiviranta, I., and Helminen, H.J., "Articular Cartilage Superficial Zone Collagen Birefringence Reduced and Cartilage Thickness Increased before Surface Fibrillation in Experimental Osteoarthritis", *Ann. Rheum. Dis.*, 57, pp. 237–245, (1998).

Gadaleta, S.J., Landis, W.J., Boskey, A.L., and Mendelsohn, R., "Polarized FT–IR Microscopy of Calcified Turkey Leg Tendon", *Connect. Tissue Res.*, 34, pp. 203–211, (1996).

Pachalis, E.P., F. Betts, E. DiCarlo, J.M. Lane, R. Mendelsohn, and A.L. Boskey, "Mineral and Organic Matrix Changes in Osteoporosis", *J. Dent. Res.*, 76, p. 287 (1997).

M. Khan, M. Yamauchi, S. Srisawasdi, D. Stiner, S. Doty, E.P. Paschalis, A.L. Boskey, "Homocysteine Decreases Chondrocyte–Mediated Matrix Mineralization in Differentiating Chick Limb–bud Mesenchymal Cell Micro–Mass Cultures", *Bone*, 28, 387–398 (2001).

Hollander, A.P., T.F. Heathfield, C. Webber, Y. Iwata, R. Bourne, C. Rorabeck, and A.R. Poole, (1994), "Increased Damage to Type II Collagen in Osteoarthritic Articular Cartilage Detected by a New Immunoassay", *Journal of Clinical Investigation*, 93, pp. 1722–1732.

Griffiths, P.R., and J.A. de Haseth, (1986), "Fourier Transform Infrared Spectrometry", *Wiley–Interscience*, New York, 457, pp. 188–193.

DETERMINATION OF THE ULTRASTRUCTURE OF CONNECTIVE TISSUE BY AN INFRARED FIBER-OPTIC SPECTROSCOPIC PROBE

CROSS REFERENCE TO RELATED APPLICATION

The present application claims the benefit of Provisional Application Ser. No. 60/204,194 filed May 12, 2000, wherein priority under 35 USC 119(e) is claimed.

BACKGROUND OF THE INVENTION

1. Field of the Invention

The present invention concerns methodology to be utilized with a probe operative in the mid-infrared or near-infrared region of the electromagnetic spectrum for the sensing of the absorption of infrared energy in a sample for the determination of the ultrastructure of connective tissue, such as soft connective tissue, such as cartilage, either in vivo or in vitro.

2. Background Information

The repair of defects in articular cartilage remains a challenging problem in orthopaedic surgery. Recently, novel tissue engineering technologies have facilitated the synthesis of cartilage-like tissue for potential implantation into defect sites. Commensurate with such developments is the requirement for new methodology to evaluate the integration of these matrices into cartilage and to assess their capability for regeneration and repair of tissue.

Fourier transform infrared ("FT-IR") spectroscopy has been used extensively to study the structure and orientation of proteins, lipids and inorganic compounds in numerous normal and pathological tissues (for review, see: *Infrared and Raman Spectroscopy of Biological Materials*, Eds. Gremlich, H. U., Yan, B., New York, Marcel-Dekker, (2001); also see Bychkov, S. M. and Kuzmina, S. A., "Study of Tissue Proteoglycans by Means of Infrared Spectroscopy", *Biull. Eksp. Biol. Med.*, 114, pp. 246–249, (1992); Camacho, N. P., Hou, L., Toledano, T. R., Ilg, W. A., Brayton, C. F., Raggio, C. L., Root, L., and Boskey, A. L., "The Material Basis for Reduced Mechanical Properties in Oim Mice Bones", *J. Bone Miner. Res.*, 14, pp. 264–272, (1999); Lazarev, Y. A., Grishkovsky, B. A., and Khromova, T. B., "Amide I Band of IR Spectrum and Structure of Collagen and Related Polypeptides", *Biopolymers*, 24, pp. 1449–1478, (1985); Liu, K. Z., Dembinski, T. C., and Mantsch, H. H., "Rapid Determination of Fetal Lung Maturity from Infrared Spectra of Amniotic Fluid",*Am. J. Obstet. Gynecol.*, 178, pp. 234–241, (1998); Mendelsohn, R., and Moore, D. J., "Vibrational Spectroscopic Studies of Lipid Domains in Biomembranes and Model Systems", *Chem. Phys. Lipids*, 96, pp. 141–157, (1998); Moore, D. J., Rerek, M. E., and Mendelsohn, R., "Lipid Domains and Orthorhombic Phases in Model Stratum Corneum: Evidence from Fourier Transform Infrared Spectroscopy Studies", *Biochem. Biophys. Res. Commun.*, 231, pp. 797–801, (1997); Moore, D. J., Gioioso, S., Sills, R. H., and Mendelsohn, R., "Some Relationships Between Membrane Phospholipid Domains, Conformational Order, and Cell Shape in Intact Human Erythrocytes", *Biochim. Biophys. Acta.*, 1415, pp. 342–348, (1999)).

The coupling of an FT-IR spectrometer to an optical microscope (FT-IR microspectroscopy ("FT-IRM")) permits quantitation of the relative amounts, molecular nature, distribution and orientation of these compounds at a spatial resolution of approximately 10 $\mu$m. Recent studies have utilized this technique to evaluate change in the mineral and organic phase in normal (Paschalis, E. P., Betts, F., DiCarlo, E., Mendelsohn, R., and Boskey, A. L., "FTIR Microspectroscopic Analysis of Normal Human Cortical and Trabecular Bone", *Calcif. Tissue Int.*, 61, pp. 480–486, (1997)) and osteoporotic human bone (Paschalis, E. P., Betts, F., DiCarlo, E., Mendelsohn, R., and Boskey, A. L., "FTIR Microspectroscopic Analysis of Human Iliac Crest Biopsies from Untreated Osteoporotic Bone", *Calcif. Tissue Int.*, 61, pp. 487–492, (1997)), in bones from mouse models of osteogenesis imperfecta (Camacho, N. P., Landis, W. J., and Boskey, A. L., "Mineral Changes in a Mouse Model of Osteogenesis Imperfecta Detected by Fourier Transform Infrared Microscopy", *Connect. Tissue Res.*, 35, pp. 259–265, (1996) and X-linked hypophosphatemia (Camacho, N. P., Rimnac, C. M., Meyer, R. A. J., Doty, S., and Boskey, A. L., "Effect of Abnormal Mineralization on the Mechanical Behavior of X-Linked Hypophosphatemic Mice Femora [published erratum appears in *Bone*, 1996 July 19(1);77], *Bone*, 17, pp. 271–278, (1995)) in turkey tendon (Gadaleta, S. J., Camacho, N. P., Mendelsohn, R., and Boskey, A. L., "Fourier Transform Infrared Microscopy of Calcified Turkey Leg Tendon", *Calcif. Tissue Int.*, 58, pp. 17–23, (1996)), and in mineralizing chick limb bud cell cultures (Boskey, A. L., Guidon, P., Doty, S. B., Stiner, D., Leboy, P., and Binderman, I., "The Mechanism of Beta-Glycerophosphate Action in Mineralizing Chick Limb-Bud Mesenchymal Cell Cultures", *J. Bone Miner. Res.*, 11, pp. 1694–1702, (1996).

A powerful enhancement to this technique has been the recent development of an infrared focal plane array detector of the FT-IR microscope. This technology enables 4096 individual spectra to be collected simultaneously over a 400×400 $\mu$m$^2$ region at 7 microns spatial resolution in less than 10 minutes; an extraordinary reduction in time and effort compared to conventional FT-IR microscopy. Moreover, infrared images based on the spatial distribution of specific molecular species in biological tissues can now easily be generated (Kidder, L. H., Kalasinsky, V. F., Luke, J. L., Levin, I. W., and Lewis, E. N., "Visualization of Silicone Gel in Human Breast Tissue Using New Infrared Imaging Spectroscopy", *Nat. Med.*, 3, pp. 235–237, (1997); Lewis, E. N., Kidder, L. H., Levin, I. W., Kalasinsky, V. F., Hanig, J. P., and Lester, D. S., "Applications of Fourier Transform Infrared Imaging Microscopy in Neurotoxicity", *Ann. N.Y. Acad., Sci.*, 820, pp. 234–247, (1997); Marcott, C., Reeder, R. C., Paschalis, E. P., Tatakis, D. N., Boskey, A. L., and Mendelsohn, R., "Infrared Microspectroscopic Imaging of Biomineralized Tissues Using a Mercury-Cadmium-Telluride Focal-Plane Array Detector", *Cell. Mol. Biol.* (*Noisy-le-grand*), 44, pp. 109–115, (1998)).

FT-IR microscopic determination of collagen orientation in articular cartilage was discussed in Camacho, N. P., Mendelsohn, R., Grigiene, R., Torzilla, P. A., "Polarized FI-IR Microscopic Determination of Collagen Orientation in Articular Cartilage", 42nd Annual Meeting, Orthopaedic Research Society, Feb. 19–22, 1996, Atlanta, Ga. FT-IR microscopic imaging of the major components of articular cartilage was discussed in "FT-IR Microscopic Imaging of Collagen and Proteoglycan in Bovine Cartilage", Camacho, N. P.; West, P.; Torzilli, P. A.; Mendelsohn, R.,*BioPolymers*, 62:1–8 (2001). FT-IR microscopic imaging analysis of bovine nasal cartilage components utilizing multivariate analysis was discussed in Potter, K., Kidder, L. H., Levin, I. W., Lewis E. N., Spencer R. G., *Arthritis & Rheum*, 44(4): 846–855 (2001).

Heretofore, articular cartilage, a connective tissue that provides resistance to compressive forces during joint movements, had not been examined in detail by conventional FT-IR spectroscopy. In its normal state, articular cartilage displays distinct microscopic zonal heterogeneity that is well-suited to FT-IRM analysis. The framework of cartilage is composed of a network of type II collagen fibrils that interact with type IX and XI collagens, non-collagenous proteins and proteoglycan (PG) components (Pelletier, J., and Martel-Pelletier, J., "The Musculoskeletal System: Articular Cartilage", Schumacher, H. R., Klippel, J. H., and Koopman, W. J., *Primer on the Rheumatic Diseases*, Atlanta: The Arthritis Foundation, pp. 8–10, (1993)).

The surface layer of tissue (superficial tangential zone) is composed of fibrils oriented parallel to the surface, presumably to minimize leakage of the tissue components (PGs and water) during loading. The midzone (or transitional zone) has been reported to have fibrils perpendicular and parallel to the surface, but also may contain fibrils in a non-specifically oriented network. The deep zone, adjacent to the bone, contains fibrils oriented parallel to the long bone axis, that may serve to strengthen the bone-cartilage junction. In addition to heterogeneity with respect to the orientation of collagen, the concentrations of individual tissue components, such as proteoglycans, vary zonally in normal cartilage.

Although both collagen (Lazarev, Y. A., Grishkovsky, B. A., and Khromova, T. B., "Amide I Band of IR Spectrum and Structure of Collagen and Related Polypeptides", *Biopolymers*, 24, pp. 1449–1478, (1985); Fraser, R. D. B. and MacRae, T. P.; *Collagen*; Horecker, B., Kaplan, N. O., Marmur, J., and Scheraga, H. A., *Conformation in Fibrous Proteins and Related Synthetic Polypeptides*, New York: Academic Press, pp. 344–402, (1973); George, A., and Veis, A., "FTIRS in $H_2O$ Demonstrates that Collagen Monomers Undergo a Conformational Transition Prior to Thermal Self-Assembly In Vitro", *Biochemistry*, 30, pp. 2372–2377, (1991); Lazarev, Y. A., Grishkovsky, B. A., Khromova, T. B., Lazareva, A. V., and Grechishko, V. S., "Bound Water in Collagen-Like Triple Helical Structure", *Biopolymers*, 32, pp. 189–195, (1992)) and proteoglycans (Bychkov, S. M., and Kuzmina, S. A., "Study of Tissue Proteoglycans by Means of Infrared Spectroscopy", *Biull. Eksp. Biol. Med.*, 114, pp. 246–249 (1992); Bychkov, S. M., Bogatov, V. N., and Kuzmina, S. A., "Infrared Spectra of Cartilage Proteoglycans", *Bull. Eksp. Biol. Med.*, 90, pp. 561–563, (1980); Bychkov, S. M., Bogatov, V. N., and Kuzmina, S. A., "Study of Different Proteoglycan Salts", *Bull. Eksp. Biol. Med.*, 92, pp. 302–305, (1981)) have been examined individually by infrared spectroscopy, but prior to the present invention, they had not been examined by IR in the intact cartilagineous tissues.

U.S. Pat. No. 5,170,056 to Berard et al. (the entire contents of which are incorporated by reference herein) concerns a probe operative in the infrared region of the electromagnetic spectrum in situ sensing of the absorption of IR energy in a sample.

U.S. Pat. No. 5,280,788 discloses an optical needle device for the diagnosis of tissues, but cartilage is not discussed therein.

U.S. Pat. No. 5,923,808 to Melling (the entire contents of which are incorporated by reference herein) describes a mid-infrared spectroscopic probe attached to a fiber-optic cable.

U.S. Pat. Nos. 5,701,913 and 6,068,604 concern probes for measuring the stiffness of cartilage or cartilage compressive properties by disposing a probe against a tissue, applying force and measuring the response to the force (the relative displacement of the probe). U.S. Pat. Nos. 5,701,913 and 6,068,604 do not involve the measurement of cartilage properties by radiation.

U.S. Pat. Nos. 5,460,182; 5,769,791; 5,785,658; 5,762,609; 5,772,597; 5,807,261 and 5,987,346 are directed to tissue penetrating devices and sensors for in vivo measurements of body tissues. Re. 36,044 concerns a diagnostic monitor for classifying an unknown biological tissue into two or more types.

SUMMARY OF THE INVENTION

It is an object of the present invention to apply methodology to be used with infrared fiber optic probe ("IFOP") technology to evaluate the ultrastructure of connective tissue including articular and meniscal cartilage, bone, ligament, tendon and capsule.

It is a further object of the present invention to employ a probe operative in the mid-infrared or near-infrared region of the electromagnetic spectrum for the sensing of the absorption of infrared (IR) energy in a sample for determination of the quality of connective tissue, such as soft connective tissue, such as cartilage, either in vivo or in vitro.

It is a still further object of the present invention to provide better treatment and management of joint diseases such as osteoarthritis, rheumatoid arthritis, osteonecrosis, and of conditions involving degenerative tissue such as those that result from traumatic injury, inflammation, infection, scarring or any response of the tissue to repair.

It is another object of the present invention to employ infrared fiber optic probe technology to enable the articular cartilage surface to be conveniently evaluated using currently available arthroscopic techniques, thus allowing in situ evaluation and quantitation of compositional and structural changes.

It is still another object of the present invention to provide in vivo monitoring of the repair of connective tissue, such as cartilage, to provide in vivo monitoring of the progression of degradation of connective tissue such as cartilage.

It is a still further object of the present invention to employ infrared fiber optic probe technology as an arthroscopic diagnostic tool for joint disease and for the evaluation of the integration of repair matrices into cartilage.

The present invention concerns a method for the evaluation of the ultrastructure of connective tissue comprising:

(a) providing a fiber optic probe operative in the mid-infrared or near-infrared region of the electromagnetic ("EM") spectrum (such as a probe described in U.S. Pat. No. 5,170,056), (b) positioning the probe to be in contact with the surface of the connective tissue for detecting attenuated total reflectance or within a sufficient distance from the surface of the connective tissue for detecting reflection, (c) detecting mid-infrared radiation or near-infrared radiation penetrating the surface of the connective tissue for detecting attenuated total reflectance or reflecting off the surface of the connective tissue for detecting reflection, and (d) analyzing the infrared radiation from step (c) for at least one of peak height, peak area and frequency and comparing at least one of the peak height, peak area and frequency to established values for at least one of peak height, peak area and frequency for normal connective tissues to detect a modification in the molecular structure of the connective tissue.

BRIEF DESCRIPTION OF THE DRAWINGS

For the purposes of illustrating the invention, there is shown in the drawings, forms which are presently preferred. It is to be understood, however, that the present invention is not limited to the precise arrangements and instrumentalities depicted in the drawings.

FIG. 7A shows the morphology of the tissue section based on total collagen content. FIG. 7B shows the orientation of the collagen, with the higher ratio indicative of fibrils oriented perpendicular to the cartilage surface. The scale for FIGS. 7A and 7B shows the range of integrated area for each pattern.

DETAILED DESCRIPTION OF THE INVENTION

Figure 1A:
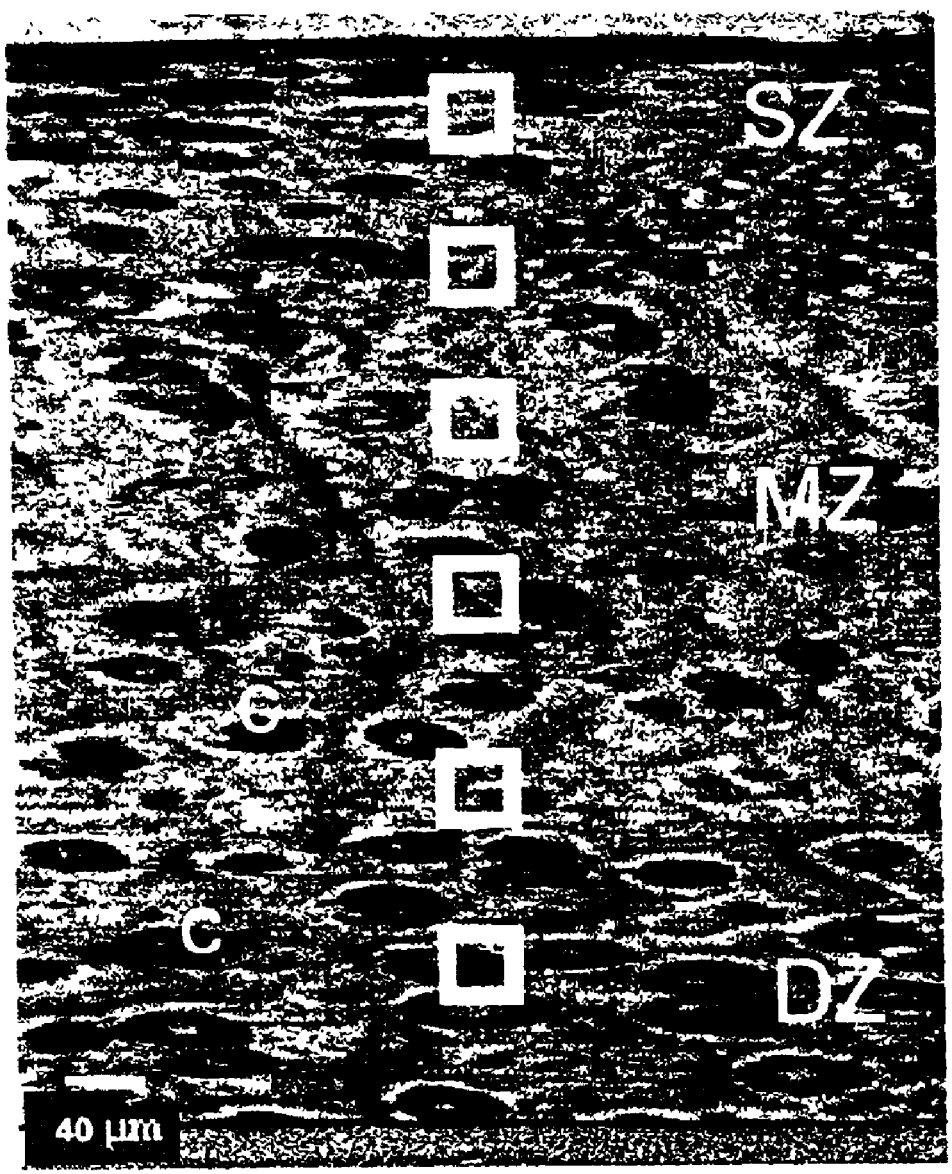
FIG. 1A shows a histological section of articular cartilage spanning the superficial zone "(SZ)", mid-zone "(MZ)" and the deep zone "(DZ)". FT-IR microscopy data was collected from regions 40×40 µm in diameter.

The present invention involves providing a fiber optic probe which is operative in the mid-infrared region of the electromagnetic spectrum (approximately 400 $cm^{-1}$ to 5,000 $cm^{-1}$) or in the near-infrared region of the electromagnetic spectrum (approximately 5,000 $cm^{-1}$ to 14,000 $cm^{-1}$). Preferably the probe operates in the mid-infrared region of the electromagnetic spectrum.

The probe for use in the present invention can detect infrared radiation by attenuated total reflectance or by reflection. In either case, the evaluation of the ultra-structure of the connective tissue can be carried out by, for example, peak shift analysis, peak area analysis or a combination of peak shift analysis and peak area analysis.

An example of a probe for use in the present invention comprises an attenuated total reflectance ("ATR") element having an input end and an output end for receiving infrared ("IR") and transmitting attenuated IR radiation, respectively (see U.S. Pat. No. 5,170,056). The infrared fiber optic probe ("IFOP") is used to evaluate the ultrastructure of connective tissues such as cartilage by examination of the IR spectrum of the connective tissue. Specific IR signature absorbance bands arise from molecular components of connective tissue such as cartilage, and changes in these bands are linked to degradation or modifications of components and thus the ultrastructure of the connective tissue, such as cartilage, can be determined.

An example of a probe for use in the present invention is as disclosed in U.S. Pat. No. 5,170,056 and is as follows:

A probe operative in the infrared region of the EM spectrum for in situ real time sensing of the absorption of IR energy in a sample comprising:

an attenuated total reflectance ("ATR") crystal element having an input end portion for receiving IR energy and an output end portion for transmitting attenuated IR energy, the ATR element having wall portions disposed along a central or long axis thereof, the IR energy being reflected along the element in a direction transverse to the central axis;

a plurality of infrared transmitting fibers in the form of a cylindrical bundle at the input end portion and the output end portion of the ATR element, the bundle of fibers having end faces disposed in direct contacting abutment with the ATR element for transmitting and receiving IR energy into and out of the element, the bundle arranged in a cluster of individual fibers, the bundle centered on an axis common with the central axis of the ATR element, the fibers having relatively high numerical apertures for spreading transmitted energy so that a portion of the energy enters the ATR element at an angle less than the critical angle for facilitating total internal reflection by the wall portions of the element and for receiving a sensible amount of IR energy from the ATR element.

In an experimental setup for attenuated total reflectance (ATR), the probe is configured with a crystal suitable for ATR such as ZnS. The crystal tip is positioned in optical contact with the surface of the sample. Infrared radiation passes through the surface of the sample, back through the fiber optic and into an infrared detector. This output signal is first measured as a function of wavelength in the absence of sample (the background spectrum); and then measured as a function of wavelength in the presence of the sample. The signal measured with sample present is then divided, point by point, by the background spectrum to give a percentage transmission, the logarithm of the percentage transmission gives the absorbance spectrum. In an experimental setup for reflection, the probe is configured without a crystal tip. It is placed a distance from the tissue that is suitable for collection of reflectance data.

A "normal" connective tissue will give rise to a signature spectrum that is comprised of absorbance peaks at specific frequencies, and of specific heights and/or areas. The spectrum of a degenerative or modified tissue will be altered from the normal, whereby there will be changes in peak height, areas, or frequencies. The present invention utilizes specific changes in peak heights, areas or frequencies to evaluate ultrastructural changes in the aforementioned connective tissues.

Preferably, a flexible fiber-optic cable comprising a mid-infrared-transmitting glass chalcogenide equipped with a MCT detector will be coupled to a spectrometer. The fiber optic will be 1 to 2 meters in length and transmissive over the infrared region of at least 400 to 4,000 $cm^{-1}$. A 5 mm diameter ZnS probe with a 1 mm region of surface contact will be attached to the end of the cable, thereby permitting sampling of 1 mm diameter sample areas. To minimize damage to the tissue, it is desirable to utilize a flat-ended ZnS crystal instead of the standard pointed design. The standard tip is a nominal two-bounce design, whereas the flat-ended design is a nominal three-bounce design. The optimum design will have the highest possible penetration depth on the flat face of the crystal, while avoiding the loss of light that will occur if an appreciable percentage of the rays exceeds the Brewster angle.

The present invention provides a method for evaluation (determination) of the ultrastructure of soft connective tissue such as articular cartilage, meniscal cartilage, ligament, tendon and capsule, or connective tissue such as bone, of a human or an animal. This evaluation can be carried out either in vivo or in vitro.

For detection by attenuated total reflectance, the infrared radiation penetrates the surface of the connective tissue to approximately up to 10 microns. For attenuated total reflectance, the probe is in contact (touches) the surface of the connective tissue. For reflection, the probe is within a sufficient distance from the surface of the connective tissue for detecting reflection (such distance could be a few centimeters from the surface of the connective tissue).

In the present invention, infrared spectral parameters are monitored in connective tissue such as cartilage, examined by infrared microscopy and imaging, and infrared fiber-optics.

Specific changes in IR bands have been discovered that are linked to the degradation of cartilage, including the following:

(a) The ratio of the integrated area and/or intensity of the collagen absorbances at 1450 $cm^{-1}$ and 1402 $cm^{-1}$ changes with cartilage degradation.

(b) The ratio of the integrated area and/or intensity of the collagen absorbances at 1550 $cm^{-1}$ (amide II) ratioed to 1450 $cm^{-1}$ band changes with cartilage degradation.

(c) The integrated area and/or intensity of the collagen absorbances at 1527 $cm^{-1}$ ratioed to the 1510 $cm^{-1}$ band changes with cartilage degradation.

(d) The integrated area and/or intensity of the collagen absorbances at 1238 $cm^{-1}$ ratioed to the 1255 $cm^{-1}$ (amide III contour) band changes with cartilage degradation.

(e) The integrated area and/or intensity of the collagen absorbances at 1238 $cm^{-1}$ ratioed to the 1227 $cm^{-1}$ (amide III contour) band changes with cartilage degradation.

(f) The integrated area and/or intensity of the collagen absorbances at 1338 $cm^{-1}$ ratioed to the 1238 $cm^{-1}$ band changes with cartilage degradation.

(g) The integrated area and/or intensity of the collagen absorbances at 1550 $cm^{-1}$ ratioed to the 1338 $cm^{-1}$ band changes with cartilage degradation.

These findings were discovered by evaluation of collagenase-degraded human and bovine cartilage, and by evaluation of human osteoarthritic cartilage.

The present invention provides FT-IRM and FT-IRI analyses of normal connective tissue such as cartilage, and identifies the specific molecular components of connective tissue such as cartilage that contribute to its infrared spectrum. As a result, a framework is provided in which complex pathological changes in this heterogeneous tissue can be assessed by infrared technology.

The present invention employing an infrared fiber optic probe ("IFOP") can be utilized as an arthroscopic diagnostic tool for joint diseases, and for evaluation of the integration of repair matrices into connective tissue such as cartilage.

Infrared spectroscopy can detect specific compositional and structural changes to connective tissue such as cartilage that occur as a result of damage or a disease state. The present invention thus can provide for acquiring IFOP data from normal and diseased connective tissue such as cartilage. A comparison of compositional and structural infrared data to that from the well-established histological methods will confirm that the IFOP is sensitive to structural changes in the connective tissue.

The infrared fiber optic probe (IFOP) can be utilized to evaluate compositional and structural changes to the chondral surface in situ. The present invention affords the development of sampling methodology such that the IFOP is placed in optical contact with cartilage specimens without causing physical damage. Reflectance IR data can also be collected without IFOP sample contact. This will permit acquisition of IFOP data from tissue samples followed by microscopic and histological examination of microstructure.

The use of the IFOP enables the molecular structure of the chondral surface to be conveniently evaluated using currently available arthroscopic techniques, thus allowing in situ detection and quantitation of compositional and structural changes in repair tissue, and in the early stages of degenerative joint disease. In addition, the availability of a hand-held instrument that would provide immediate information on cartilage molecular integrity would assist a surgeon in determination of how to proceed at surgery.

The present invention is based on the identification of the primary constituents of connective tissue such as articular cartilage by infrared spectral analysis. Spectral absorbances that arise from type II collagen and proteoglycan were identified, and semi-quantitative information measured from these components. In addition, orientation information was obtained through the use of polarization experiment.

This is a powerful employment of infrared technology that is useful for detection of compositional and structural changes to connective tissue such as cartilage that occur as a result of disease state or mechanical damage. For example, a significant complication in the treatment of osteoarthritis is the inability to diagnose the disease process at an early stage. While macroscopic, later-stage damage such as lacerations, ruptures and chondral fractures can be recognized via existing technology (Buckwalter, J. A., and Mow, V. C., "Injuries to Cartilage and Meniscus: Sports Injuries to Articular Cartilage", DeLee, J. C., and Drez, D., Jr., *Orthopaedic-Sports Medicine Principles and Practice*, Philadelphia: W. B. Saunders Company, pp. 82–107, (1994)), early stages of osteoarthritis that involve breakdown of matrix molecules, but no obvious mechanical damage are much more difficult to identify. Recent advances in magnetic resonance imaging ("MRI") permit direct visualization of cartilage and identification of lesions (Potter, H. G., Linklater, J. M., Allen, A. A., Hannafin, J. A., and Haas, S. B., "Magnetic Resonance Imaging of Articular Cartilage in the Knee: An Evaluation With Use of Fast-Spin-Echo Imaging", *J. Bone Joint, Surg.*

Am., 80, pp. 1276–1284 (1998); Recht, M. P., and Resnick, D., "Magnetic Resonance Imaging of Articular Cartilage: An Overview" *Top. Magn. Reson. Imaging,* 9, pp. 328–336 (1998)), but specific identification of early molecular changes, such as collagen or proteoglycan breakdown, is not feasible. Identification of these changes will provide the most significant clues to the mechanism of early chondral degeneration, and can potentially be detected by FT-IR spectroscopy.

In agreement with histological studies (Speer, D. P., and Dahners, L., "The Collagenous Architecture of Articular Cartilage, Correlation of Scanning Electron Microscopy and Polarized Light Microscopy Observations", *Clin. Ortho.,* 167, pp. 267–275, (1979)), the polarization experiments discussed hereinbelow showed a gradual increase in alignment of the collagen molecules with the long axis of bone, i.e., perpendicular to the chondral surface, upon progression from the superficial to the deep zone of cartilage. In addition, the fibrils in the superficial zone displayed alignment parallel to the chondral surface. The demonstrated sensitivity of IR to collagen orientation in cartilage thus can be an indicator of early tissue pathology, since breakdown of collagen molecules in diseases like osteoarthritis, is accompanied by changes in fibril alignment (Panula, H. E., Hyttinen, M. M., Arokoski, J. P., Langsjo, T. K., Pelettari, A., Kiviranta, I., and Helminen, H. J., "Articular Cartilage Superficial Zone Collagen Birefringence Reduced and Cartilage Thickness Increased before Surface Fibrillation in Experimental Osteoarthritis", *Ann. Rheum. Dis.,* 57, pp. 237–245, (1998)).

Some advantages of the present invention are that complex pathological changes in connective tissue such as cartilage could be evaluated at an earlier stage than is currently possible, and that integration of repair tissue into existing connective tissue such as cartilage could be evaluated. Overall, the study, diagnosis and treatment of a range of chondral diseases would be greatly facilitated.

EXAMPLES

Example 1

Cartilage Tissues

Full-depth cartilage explants were harvested from adult bovine occipital joints (obtained from local slaughter house) immediately after death. Six explants from two adult animals were examined. The tissues were removed from subchondral bone with a scalpel, and circular plugs (typically 0.5 to 1 mm thick) cut with an 8 mm diameter biopsy punch. The plugs were then snap-frozen in liquid nitrogen and stored at −70° C. For FT-IRM and FT-IRI analysis, the cartilage plugs were infiltrated with OCT embedding media (Miles Inc., Elkhart, Ind.) to facilitate sectioning, crysectioned at 6 $\mu$m thickness perpendicular to the articular surface, transferred to a $BaF_2$ window and air-dried. Residual OCT in the tissue was dissolved with a few drops of water and the section re-dried.

Example 2

Model Compounds

Aliquots of chick type II collagen (Genzyme, Boston, Mass.) and purified calf nasal aggrecan were analyzed by FTIR and KBr pellets (2 mg sample: 200 mg KBr) using a Mattson Cygnus 25 Infrared Spectrometer (Mattson Instruments, Madison, Wis.). Ten sets of KBr pellets containing mixtures of type II collagen and aggrecan in varying proportions were also analyzed. The spectrum of liquid water was obtained by placing a drop of distilled water between two barium fluoride windows. Absorbance spectra were obtained by the co-addition of 256 interferograms collected at 4 cm resolution, followed by the Fourier transform of the resultant interferrogram.

Example 3

FT-IRM Analyses

A Bio-Rad (Cambridge, Mass.) FTS-40 infrared spectrometer coupled to a Bio-Rad UMA 500 microscope equipped with a mercury-cadmium-telluride ("MCT") detector was used to acquire data at 4 $cm^{-1}$ resolution under $N_2$ purge. To obtain information on collagen and proteoglycan content and distribution, spectra of regions ranging from 20×20 $\mu$m to 40×40 $\mu$m diameter were acquired from all zones of cartilage. Typically, approximately 5 spectra per region of tissue analyzed were acquired.

To obtain information on the orientation of the collagen fibrils, polarization data was collected. A wire grid infrared polarizer was placed between the $BaF_2$ window containing the tissue section and the impinging IR radiation. Spectral data was collected with infrared radiation polarized parallel and perpendicular to the cartilage articular surface. All data analyses were performed using Grams/32 software (Galactic Industries, Salem, N.H.).

Example 4

FT-IRI Analyses

A Bio-Rad (Cambridge, Mass.) FTS-60A step-scanning Stingray 6000 FTIR spectrometer with a UMA 300A FTIR microscope and a 64×64 MCT FPA detector was used to acquire spectra at 8 $cm^{-1}$ resolution under a $N_2$ purge. Data were collected from a 400×400 $\mu m^2$ region at 64×64 individual points of 7 $\mu$m diameter, resulting in 4096 individual spectra. Polarization data were acquired by placement of a wire grid polarizer between the sample and the impinging infrared radiation. Spectra were acquired with infrared radiation polarized parallel and perpendicular to the articular surface.

All imaging data were analyzed in WinIR Pro software (Bio-Rad). The areas of the amide I and II absorbances and the proteoglycan absorbances were calculated for each spectrum between 1710–1595, 1595–1510, and 960–1185 $cm^{-1}$, respectively. Infrared images were then created based on these absorbances. For the polarization data, it was assumed that the amide I absorbance arises primarily from the C=O (carbonyl) stretching vibration of the type II collagen and was oriented approximately perpendicular to the collagen fibril long axis. Since the amide I and amide II absorbances have inverse polarizations (Gadaleta, S. J., Landis, W. J., Boskey, A. L., and Mendelsohn, R., "Polarized FT-IR Microscopy of Calcified Turkey Leg Tendon", *Connect. Tissue Res.,* 34, pp. 203–211, (1996)), the ratio of the areas of amide I: amide II absorbances in one polarization (perpendicular to the articular surface) was calculated and imaged as an indicator of orientation. For this case, a larger amide I:amide II ratio represents collagen fibrils oriented parallel to the cartilage articular surface. The total area of the amide I plus amide II was imaged to show the collagen distribution in the polarized sections.

Results for Examples 1 to 4

Cartilage and Model Compounds

Figure 1B:
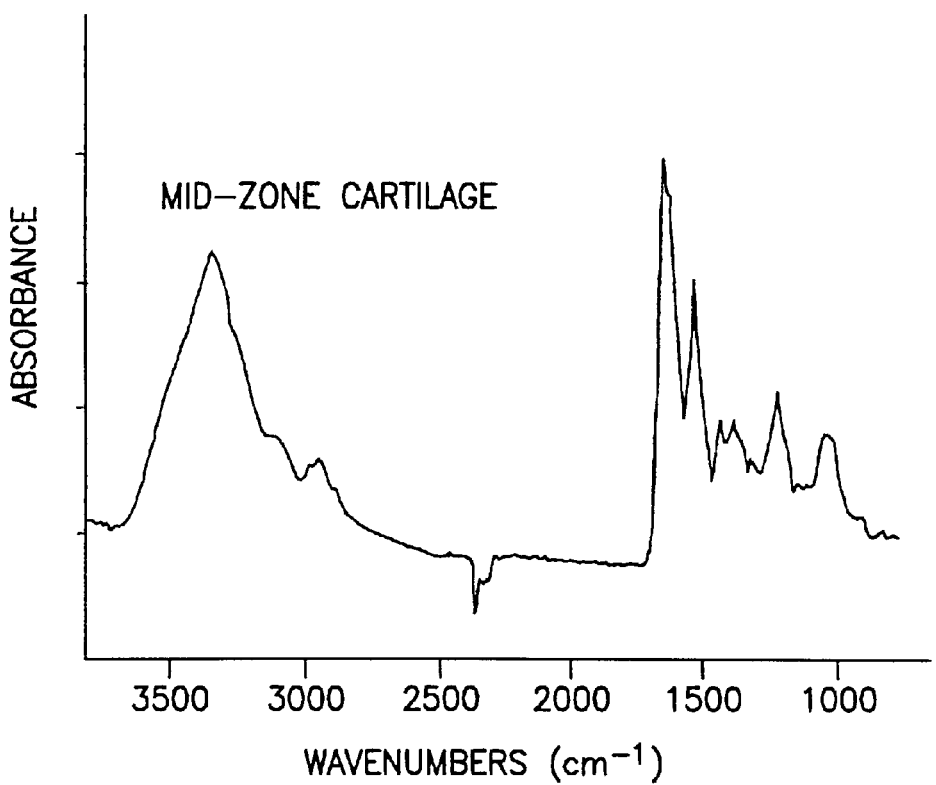
FIG. 1B shows a typical FT-IR microscopy spectrum obtained from mid-zone cartilage.
Figure 2:
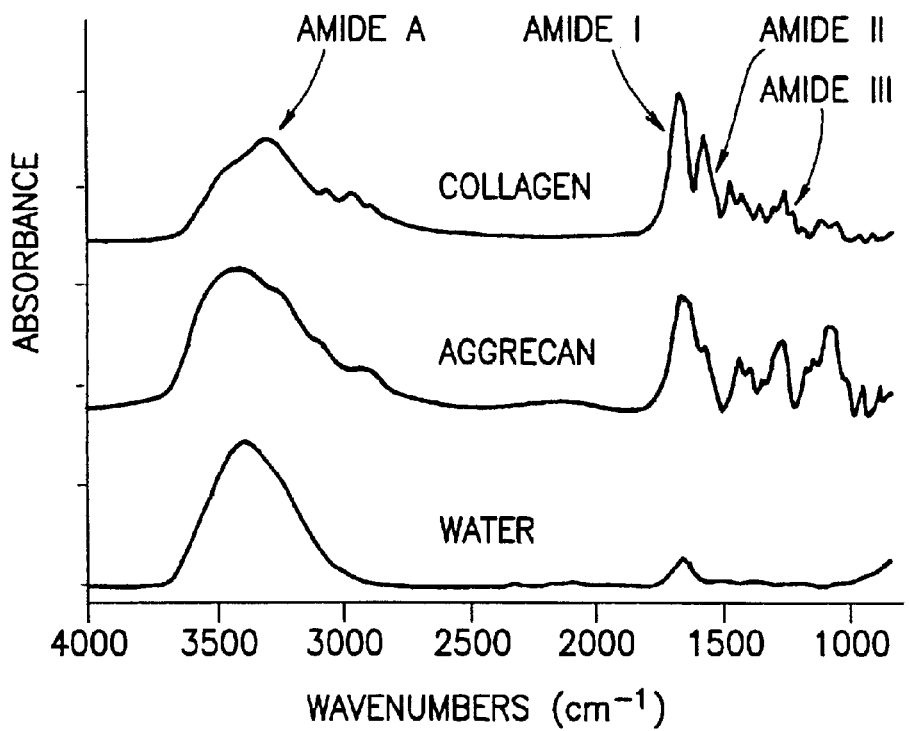
FIG. 2 depicts FT-IR spectra of the model compounds type II collagen, aggrecan and water.
Figure 3A:
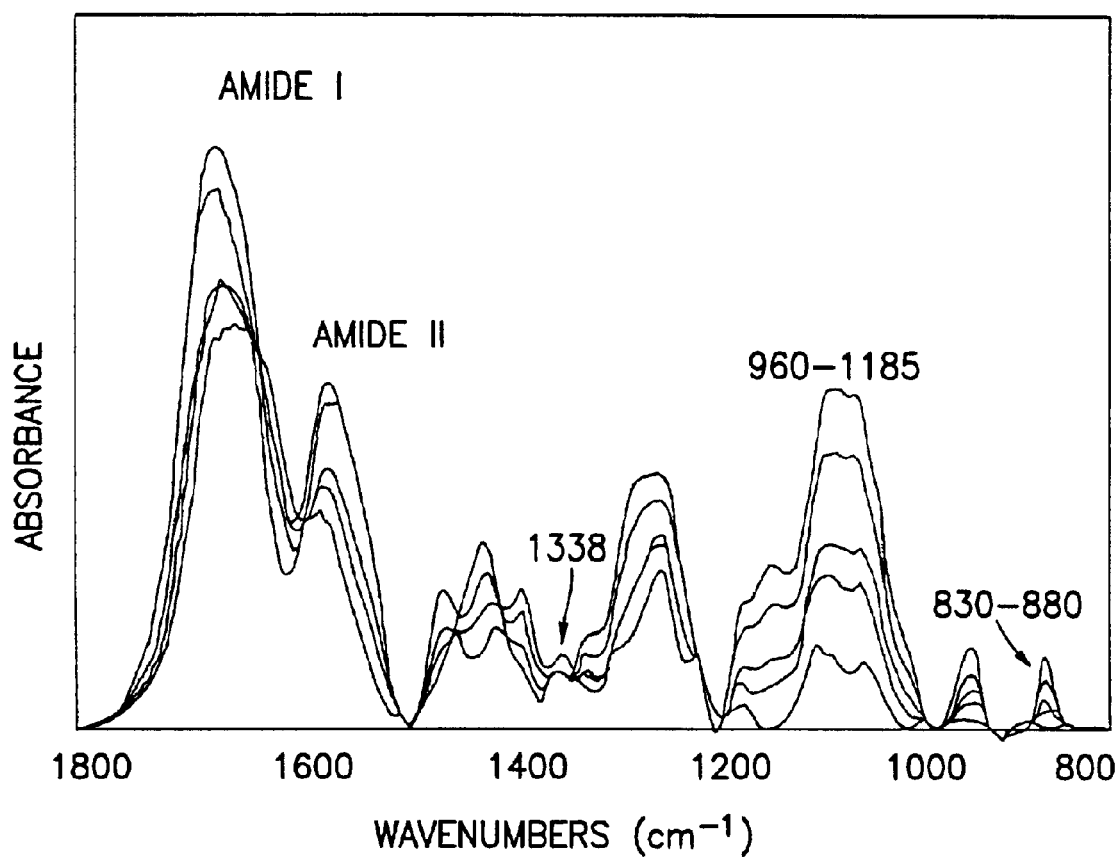
FIGS. 3A to 3G show FT-IR spectra and peak analysis from KBr pellets of mixtures of type II collagen and the proteoglycan aggrecan. The shift in peak position of the amide I (FIG. 3B) and amide II (FIG. 3C) absorbances was directly related to the quantity of collagen in the mixture (inversely related to the quantity of aggrecan). The integrated area of the 960–1185 $cm_{-1}$ sugar absorbance (FIG. 3D) and the 830–880 $cm^{-1}$ sulfate absorbance (FIG. 3E) was directly related to the quantity of aggrecan in the mixture. The integrated area of the amide I (1710–1595 $cm^{-1}$) (FIG. 3F) and 1338 collagen absorbance (FIG. 3G) was inversely related to the quantity of aggrecan (directly related to the quantity of collagen) in the mixture.
Figure 3B:
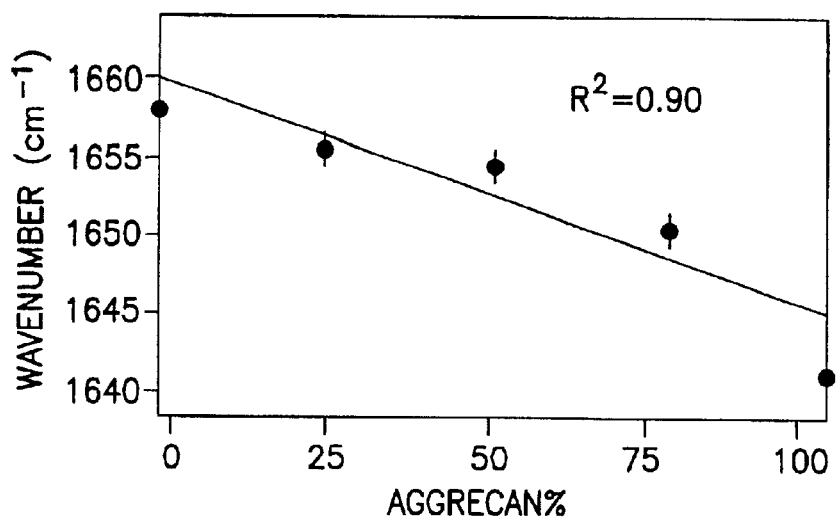
Figure 3C:
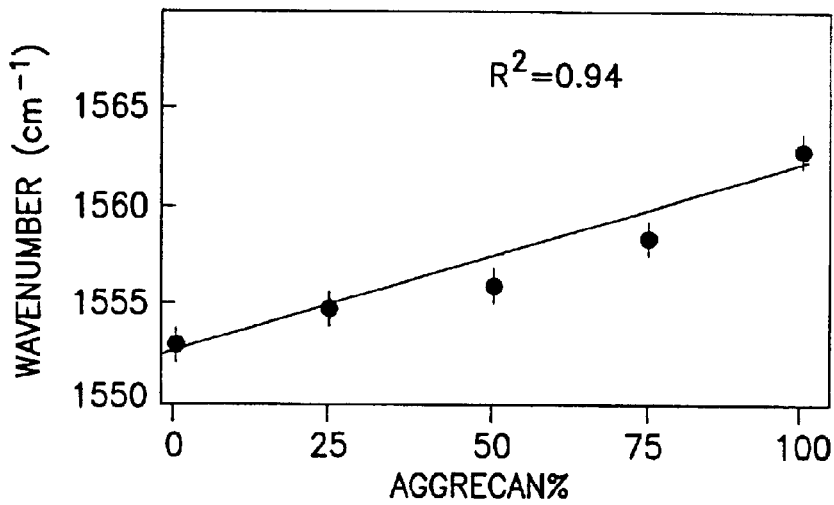
Figure 3D:
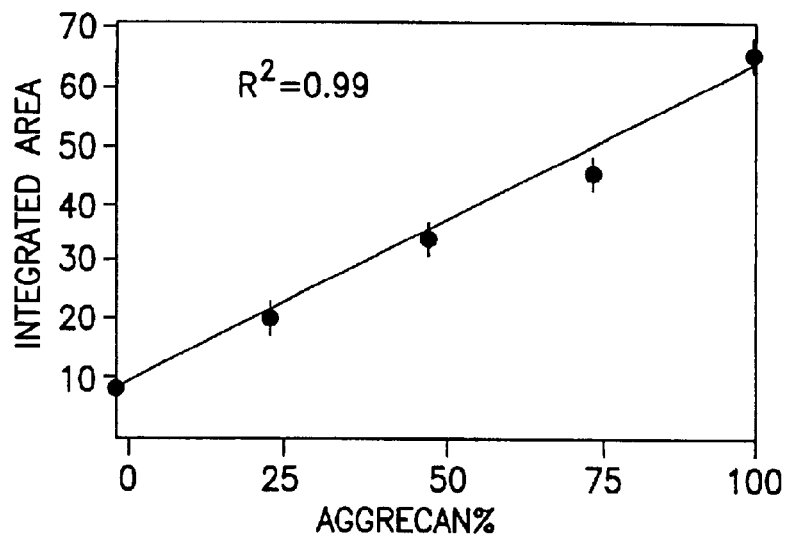
Figure 3E:
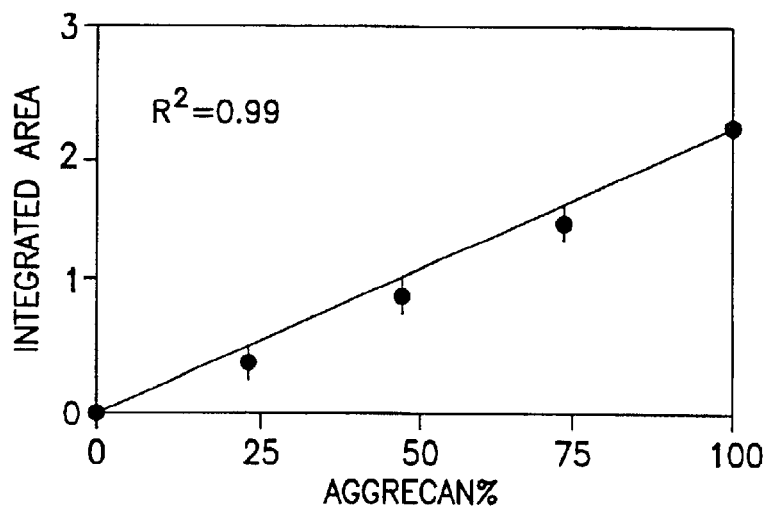
Figure 3F:
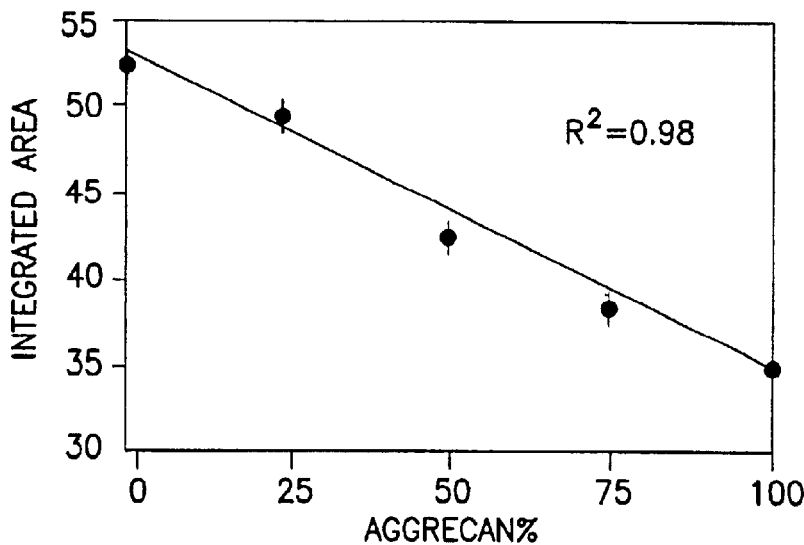
Figure 3G:
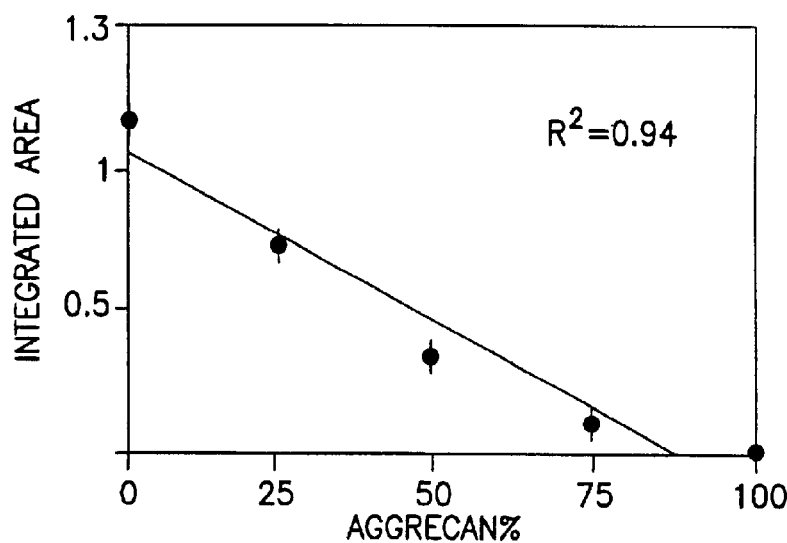

FT-IRM (FIG. 1B) spectra were obtained from the superficial, mid and deep zones of articular cartilage sections (FIG. 1A). Comparison to spectra from the model compounds type II collagen, aggrecan, and water (FIG. 2) was necessary to interpret the absorbances. The primary absorbances attributed to collagen molecules arise from the following carbonyl group containing compounds: Amide A, I, II and III (Table I).

TABLE I

Infrared Frequencies of Collagen*, Proteoglycans and Water*

| Collagen Bond Vibrations | Frequency (cm$^{-1}$) |
|---|---|
| Amide A N=H stretch | 3330 |
| Amide I C=O stretch | 1655 |
| Amide II C—N stretch, N—H bend combination | 1550 |
| Amide III C—N stretch, N—H bend, C—C stretch | 1250 |

| Proteoglycan Bond Vibrations | Frequency (wavenumber) |
|---|---|
| Amide I C=O stretch | 1640 |
| Amide II C—N stretch, N—H bend combination | 1545 |
| Sulfate stretch | 1245 |
| C—O—C, C—OH, C—C ring vibrations | 1125–920 |
| C—O—S stretch | 850 |

| Water Bond Vibrations | Frequency (wavenumber) |
|---|---|
| O—H stretch | 3700–3200 |
| H—O—H bending | 1640 |

*Fraser, R.D.B., and McRae, T.P.; Collagen; Horecker, B., Kaplan, N.O., Marmur, J., and Scheraga, H.A., "Conformation in Fibrous Proteins and Related Synthetic Polypeptides", New York: Academic Press, pp. 344–402, (1973)
**Bychkov S.M., and Kuz'mina, S.A., "Study of Tissue Proteoglycans by Means of Infrared Spectroscopy", Biull. Espk. Biol. Med., 114, pp. 246–249, (1992); Bychkov, S.M. Bogatov, V.N., and Kuzmina, S.A., "Infrared Spectra of Cartilage Proteoglycans", Biull. Eksp. Biol. Med., 90, pp. 561–563, (1980); Bychkov, S.M., Bogatov, V.N., and Kuzmina, S.A., "Study of Different Proteoglycan Salts", Biull. Eksp. Biol. Med., 92, pp. 302–305, (1981)
***Lazarev, Y.A., Grishkovsky, B.A., Khromova, T.B., Lazareva, A.V., and Grechishko, V.S., "Bound Water in Collagen-Like Triple Helical Structure", Biopolymers, 32, pp. 189–195 (1992)

The spectrum of aggrecan, a proteoglycan that contains chondroitin and keratin sulfate molecules linked to a protein core, exhibits absorbances that arise from the sulfate, sugar, and protein entities. The spectrum of liquid water exhibits absorbances from the O—H bond stretching and bending modes. However, O—H bending vibration of water at 1640 cm$^{-1}$ exhibits an absorbance of at least 10-fold less than the stretching vibration at approximately 3300 cm$^{-1}$, and the contribution of water in the amide I region of the spectra could thus be considered negligible for these cartilage samples.

Since the spectra of isolated type II collagen and aggrecan displayed considerable overlap, it was necessary to analyze mixtures of these two compounds to determine the best way to quantitate the individual components in cartilage (FIGS. 3A to 3G). Upon increasing the ratio of aggrecan to collagen, several successive changes were noted in the spectra of the collagen-aggrecan mixtures. The primary changes that were potentially suitable as quantitative indicators were the shift in the amide I and amide II absorbances from approximately 1660 to 1643 cm$^{-1}$ (FIG. 3B) and approximately 1553 to 1564 cm$^{-1}$ (FIG. 3C) and the integrated areas of the 960–1185 cm$^{-1}$ (FIG. 3D) and the 830–880 cm$^{-1}$ (FIG. 3E) absorbance regions. It was also determined that the areas of the amide I band (1710–1595 cm$^{-1}$) (FIG. 3F) and the absorbance centered at 1338 cm$^{-1}$ (FIG. 3G) were directly correlated to the quantity of type II collagen in the mixtures.

Mapping and Imaging

Figure 4:
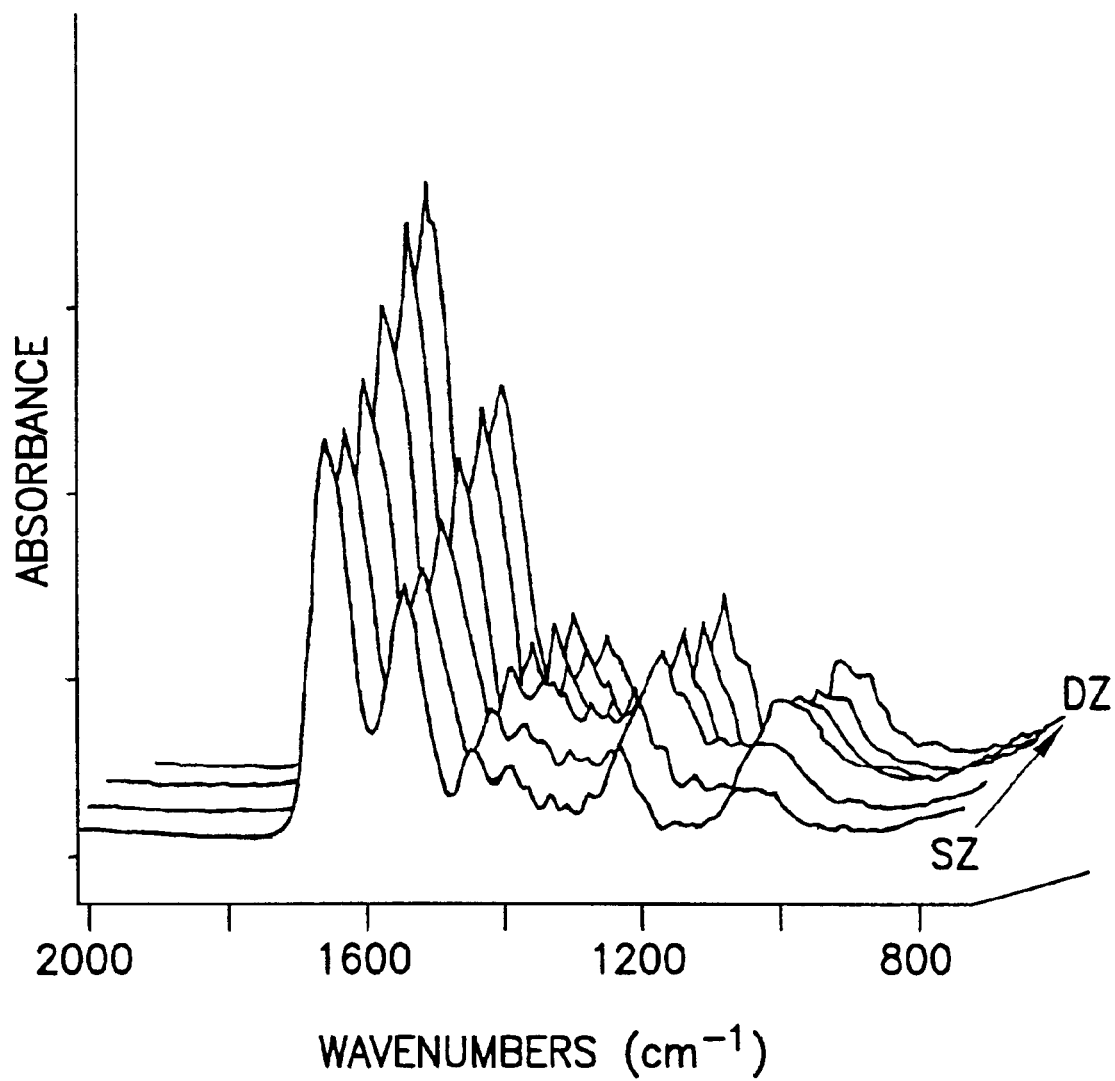
FIG. 4 shows a FT-IR microscopy spectral map obtained at 50 µm intervals through the superficial mid and deep zones of bovine articular cartilage.
Figure 5A:
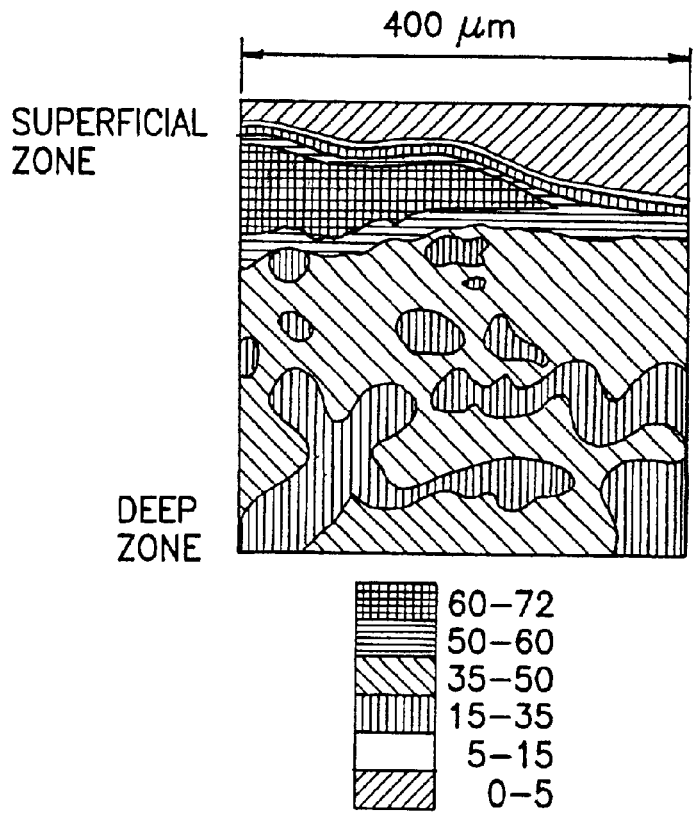
FIGS. 5A to 5C depict FT-IRI images of collagen and proteoglycan in bovine articular cartilage. The collagen image (FIG. 5A) was created based on the area of the amide I absorbance, and the proteoglycan images created based on the area of the 960–1185 $cm^{-1}$ absorbance ratioed to the area of the 1338 $cm^{-1}$ absorbance (FIG. 5B) and the amide I absorbance (FIG. 5C). The scale for FIGS. 5A to 5C shows the range of integrated area for each pattern.
Figure 5B:
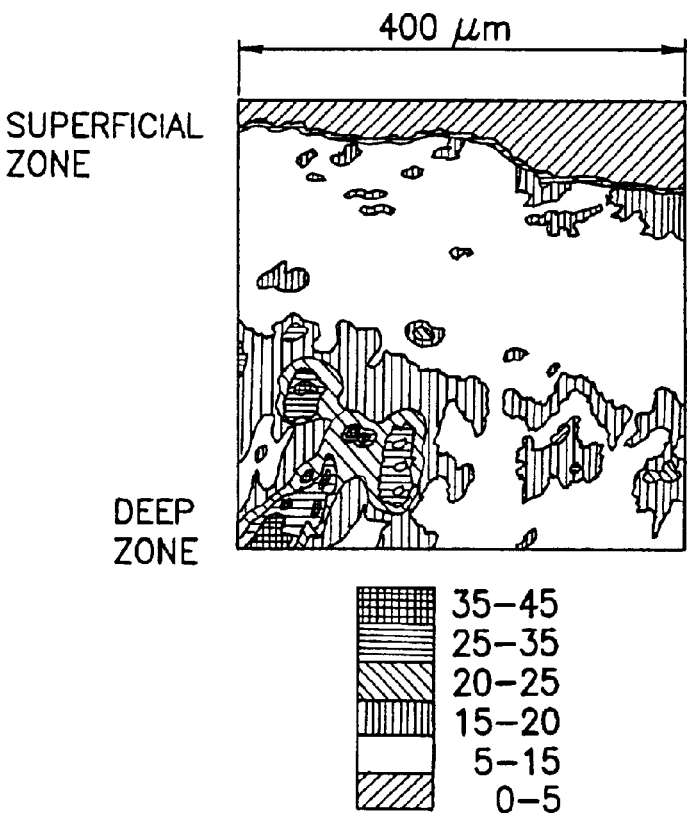
Figure 5C:
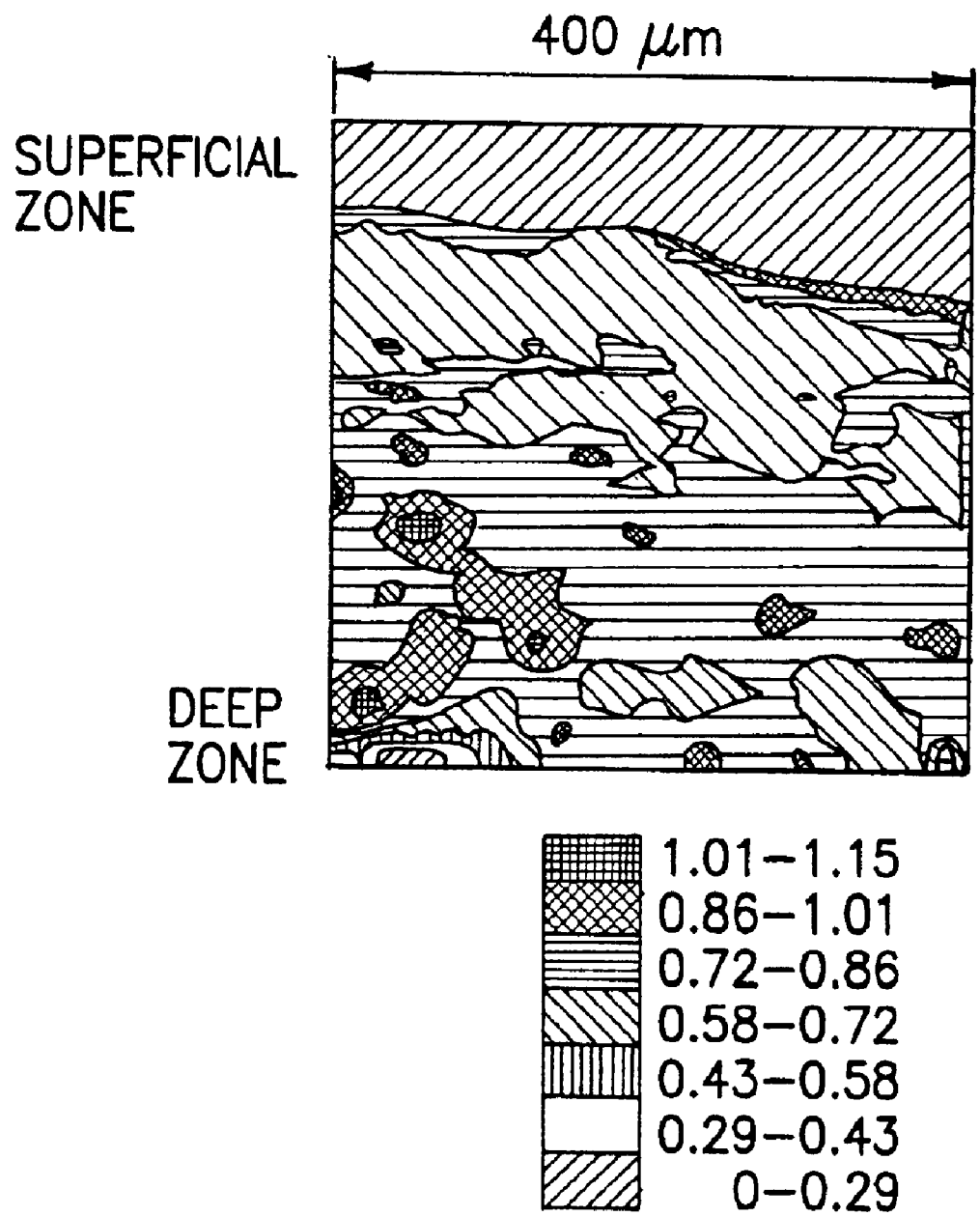

An FT-IRM "spectral map" acquired at 50 μm intervals through the superficial, mid and deep zones of thin sections of bovine articular cartilage shows variation in intensities of the absorbance bands that arise from the collagen and aggrecan components, and thus reflect differences in quantity of these specific components (FIG. 4). FT-IRI was utilized to image the individual components in another section of cartilage (FIG. 5). It is clear from these images that the greatest density of collagen corresponds to the superficial tangential zone, in agreement with histological studies (FIG. 5A). Proteoglycan, imaged based on the 960–1185 cm$^{-1}$ absorbance ratio to the 1338 cm$^{-1}$ collagen amide I (FIG. 5B) and to the amide I peak (FIG. 5C) varies substantially throughout the tissue, but is clearly weakest in the superficial zone.

Polarization Data

Figure 6B:
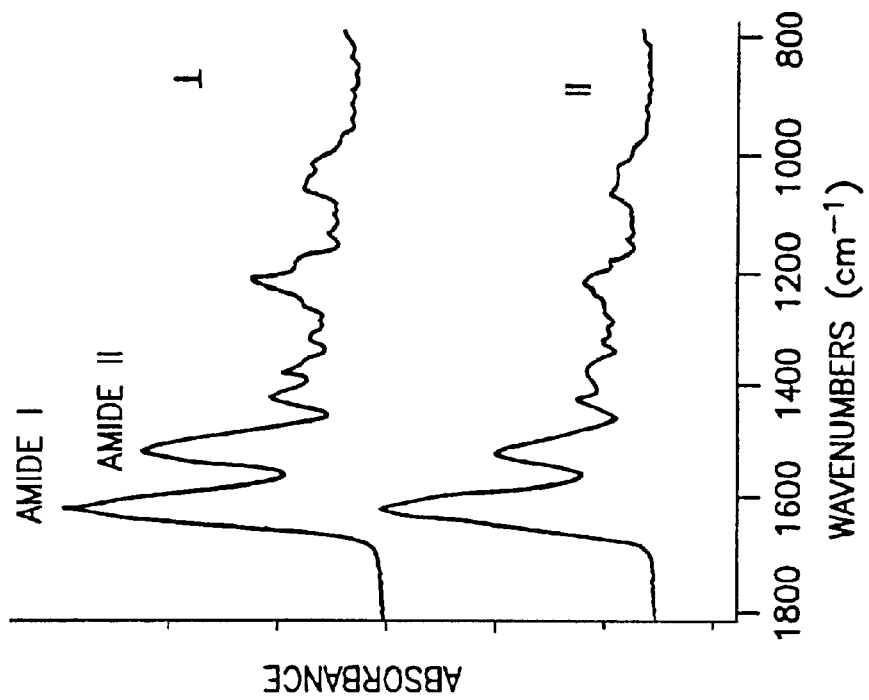
FIGS. 6A and 6B show polarized FT-IRM spectra from the superficial (FIG. 6A) and deep zones (FIG. 6B) of cartilage. Spectral data were collected with infrared radiation polarized perpendicular (top—⊥) and parallel (bottom—∥) to the cartilage articular surface. The amide I and II bands display opposite polarizations within the same spectrum. In addition, the intensity of these absorbances change zonally, indicative of changes in average orientation of the collagen molecules.
Figure 6A:
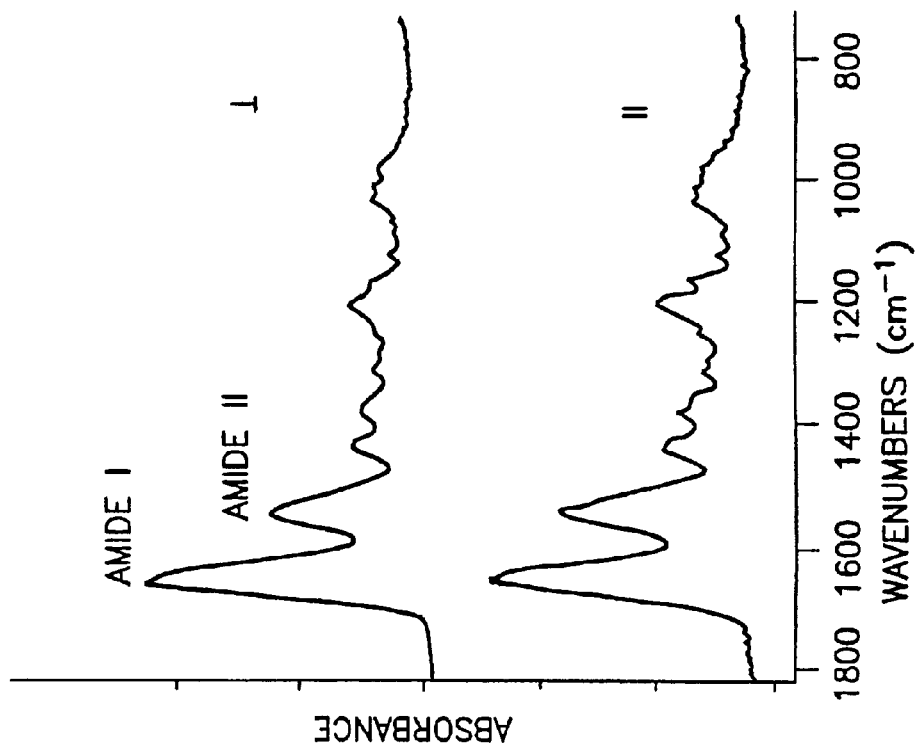
Figure 7A:
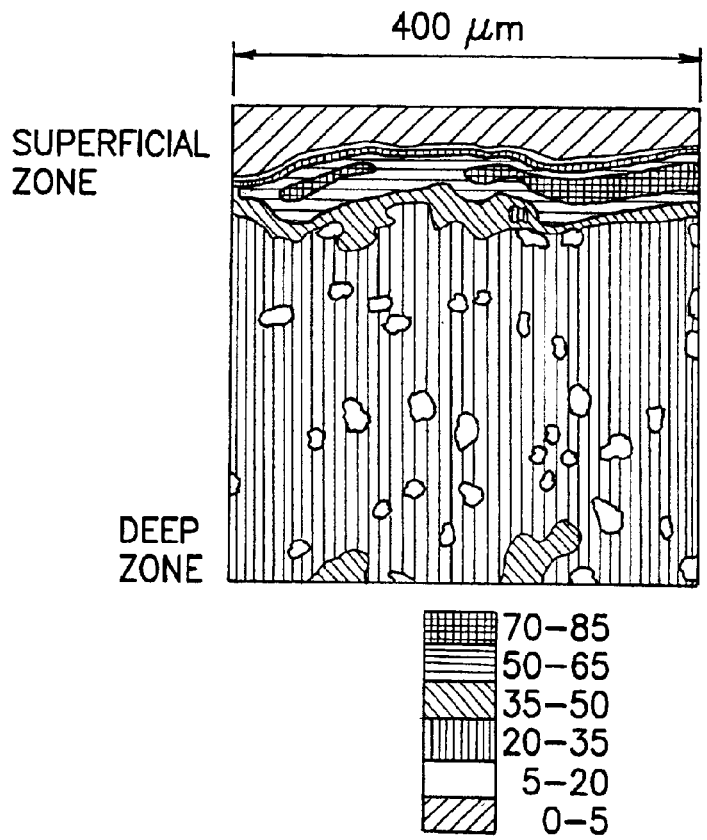
FIGS. 7A and 7B show polarized FT-IR images of bovine articular cartilage based on (FIG. 7A) amide I and amide II and (FIG. 7B) amide I:amide II.
Figure 7B:
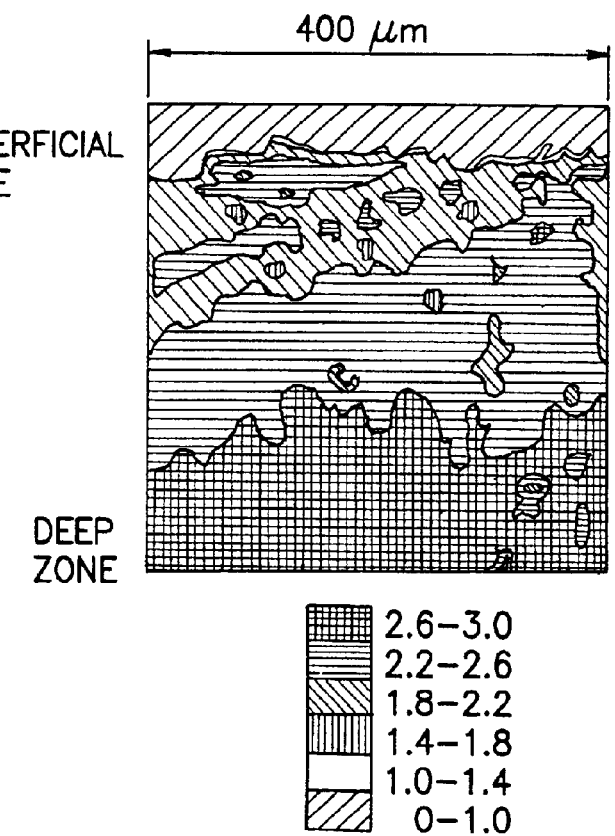

Polarized FT-IRM spectra from the superficial (FIG. 6A) and deep zones (FIG. 6B) of cartilage showed different intensities of the collagen absorbances, particularly the amide I and II bands, indicative of changes in average orientation of the collagen molecules. The spectra from the midzone did not show any obvious polarization. FT-IRI was utilized to image the orientation of the collagen fibrils based on the amide I:amide II ratio (FIG. 7B). With this technique, the zonal differences in orientation were readily apparent. The collagen fibril orientation changed gradually from parallel to the articular surface in the superficial zone, to perpendicular to the articular surface in the deep zone.

Example 5

Figure 8:
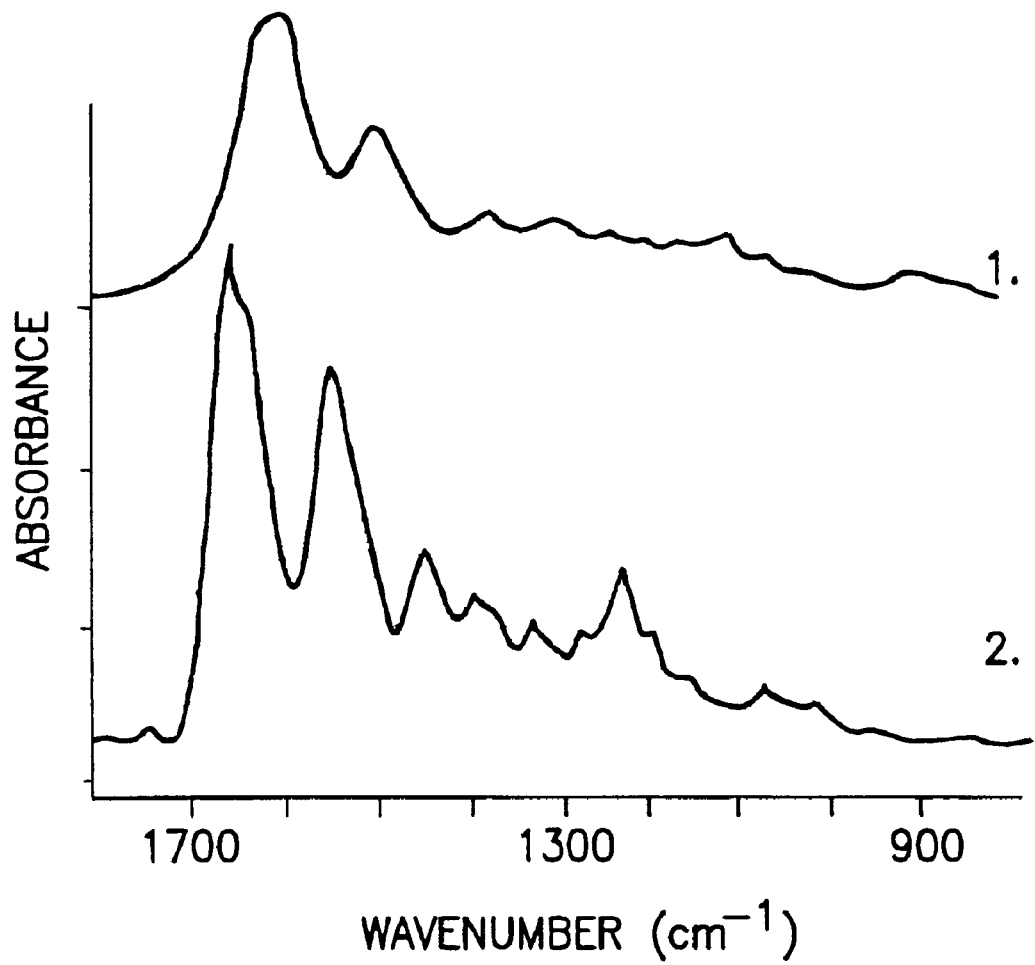
FIG. 8 are spectra that show fiber optic probe data from human osteoarthritic cartilage (1), and an IR spectrum of collagen (2).

To determine the feasibility of acquiring infrared fiber optic probe (IFOP) data from harvested cartilage samples, human cartilage harvested during joint arthroplasty were examined. Osteoarthritic and normal articular cartilage were obtained during the course of joint arthroplasties. The tissue was placed in sterile saline and stored at 4.C. until the time of analysis. The probe was greatly pressed on the cartilage blocks during data acquisition, and 512 scans collected and co-added. FIG. 8 shows IFOP data from human osteoarthritic cartilage (1) which is similar to the spectrum of type II collagen (2). A slight indentation in the tissue after sampling was noticed, possibly indicative of microscopic damage. Nonetheless, the feasibility of examining harvested cartilage tissue by infrared fiber optic was demonstrated.

To further evaluate the feasibility of using the IFOP to determine cartilage integrity, IFOP data was collected from sites in the harvested human cartilage tissue visually identified as grossly normal (no obvious macroscopic damage, grade 1) and degraded (fibrillations, cleft or fissures present, grade 3). Spectra of grade 1 vs. grade 3 cartilage obtained by IFOP were compared. Spectral data analysis revealed a trend of decreasing peak ratios for grade 1 vs. grade 3 for ratios 1527/1510 cm$^{-1}$, 1449/1402 cm$^{-1}$, 1238/1255 cm$^{-1}$, 1238/1227 cm$^{1}$, and 1338/1238 cm$^{-1}$, 1449/1402 cm$^{-1}$, 1238/1255 cm$^{-1}$, 1238/1227 cm$^{-1}$, and 1338/1238 cm$^{-1}$. There was also an increase in the area ratio of the 1550/1338 cm$^{-1}$ from grade 1 to grade 3 cartilage.

Example 6

Experimental Design

Prior to collection of IFOP data, a series of experiments will be conducted utilizing the FT-infrared imaging (FT-IRI) spectrometer. FT-IRI allows for collection of data from histological sections at 7 microns spatial resolution. Thus, this set of experiments will permit correlation of infrared data with traditional histological assays. The tissues described below will be utilized both for FT-IRI and for IFOP.

Tissues

Human articular cartilage with varying degrees of osteoarthritis will be analyzed, such as from joint arthroplasties and trauma surgeries. It is estimated that approximately 5 tissues from each stage of osteoarthritis will be available for analysis. The grade (or stage) of chondromalacia from harvested tissues is routinely evaluated according to Collins-Mankin histopathologic classification (Collins, D. H., (1949), "Osteoarthritis: in the Pathology of Articular and Spinal Diseases", D. H. Collins, editor, Edward Arnold, London, 74–155). In addition, approximately five tissues from "normal" cartilage obtained from trauma surgeries such as radial head fractures will be available. All harvested cartilage will be flash-frozen in liquid nitrogen. Tissues for histological and FT-IRI evaluation will be cyro-sectioned at a thickness of 6 microns.

Bovine occipital cartilage will also be utilized to evaluate physical damage caused by the IFOP during sampling. The cartilage will be obtained from a local slaughterhouse.

Analyses: FTIR Micro-Spectroscopic Imaging ("FT-IRI") Data Acquisition & Analysis To compare infrared information directly to histology data, some tissues will be examined by FT-IRI in addition to IFOP. Data will be acquired from the cryosectioned tissues. A Bio-Rad (Cambridge, Mass.) UMA 300A FTIR microscope with an FTS-60A step-scanning FTIR spectrometer and a 64×64 MCT FPA detector (Stingray Imaging Spectrometer) will be used to acquire data at 8 $cm^{-1}$ resolution under a $N_2$ purge. This allows information on collagen integrity and cross-links, and proteoglycan content and distribution to be obtained from a 400×400 $\mu m^2$ region at 64×64 individual points of 5 to 7 $\mu m$ diameter, resulting in 4,096 individual spectra. The FT-IRI data will be correlated with established morphological, histological, and immunohistochemical diagnostic parameters.

Integrated areas of infrared absorbance bands are proportional to the quantity of a specific component present. Thus, the areas of the collagen amide I absorbance (1595–1720 $cm^{-1}$) and the proteoglycan ("PG") sugar ring absorbances (980–1160 $cm^{-1}$) will be calculated at specific points to obtain a quantitative measure of collagen and PG content. These data will be compared to standard histological data for type II collagen and proteoglycan.

The amide I region of collagen has three primary underlying components that contribute to the broad absorbance contour. Recently, studies have linked changes in the areas of these components to changes in integrity and possibly cross-links of the collagen fibrils (Pachalis, E. P., F. Betts, E. DiCarlo, J. M. Lane, R. Mendelsohn, and A. L. Boskey, (1997), "Mineral and Organic Matrix Changes in Osteoporosis", *J. Dent. Res.,* 76, p. 287; M. Khan, M. Yamauchi, S. Srisawasdi, D. Stiner, S. Doty, E. P. Paschalis, A. L. Boskey, (2001), "Homocysteine Decreases Chondrocyte-Mediated Matrix Mineralization in Differentiating Chick Limb-bud Mesenchymal Cell Micro-Mass Cultures", Bone, in press). A similar protocol will be utilized in the current study to evaluate the integrity of the type II collagen fibrils in cartilage. This data will be compared to immunohistochemical data sensitive to damaged type II collagen fibrils (Hollander, A. P., T. F. Heathfield, C. Webber, Y. Iwata, R. Bourne, C. Rorabeck, and A. R. Poole, (1994), "Increased Damage to Type II Collagen in Osteoarthritic Articular Cartilage Detected by a New Immunoassay", *Journal of Clinical Investigation,* 93, pp. 1722–1732).

Statistical & Outcome Analysis

To establish that the FT-IRI data correlates with the histological data, univariate statistics will be collected on all variables. Correlation coefficients for related measurements will be obtained based on location in tissue samples. For example, FT-IRI measure of proteoglycan content at a specific location, will be compared to the histological evaluation, i.e., intensity of stain, at the parallel location in the tissue.

Infrared Fiber Optic Probe (IFOP)

A flexible fiber optic cable composed of the mid-infrared-transmitting glass "halogenide" (RemSpec Corp., Sturbridge, Mass.) equipped with an MCT detector will be coupled to the Mattson Cygnus 25 spectrometer (Mattson Instruments, Madison, Wis.). The fiber optic is 1 meter in length and transmissive over the infrared region of 4000–900 $cm^{-1}$. A 5 mm diameter probe with a 1 mm region of surface contact will be attached to the end of the cable, thereby permitting sampling of 1 mm diameter sample areas. The needle probe uses "attenuated total reflectance" (ATR) technology, whereby the radiation passes through the surface of the sample to a maximum depth of approximately 10 microns (Griffiths, P. R., and J. A, de Haseth, (1986), "Fourier Transform Infrared Spectrometry", *Wiley-Interscience,* New York, 457, pp. 188–193). Thus, data is obtained from the extreme top layer of the tissue.

Development of Data Acquisition Techniques

Initial data will be acquired from intact, normal cartilage samples (from 5 to 10 mm in size) obtained from trauma surgeries, and from bovine cartilage. To optimize surface and optical contact, sampling with varying amounts of pressure will be investigated on approximately 10 tissues. The tissues will first be secured on an adjustable-height platform, either mechanically or by gluing. Then, the fiber optic will be gently pressed on the tissue for data acquisition. Slight increases in the height of the platform will produce increased amounts of pressure and stress on the sample. These will be monitored through the use of a calibrated load cell. Infrared data on collagen and proteoglycan content, distribution, and integrity will be acquired from the chondral surface. The tissues will then be flash-frozen in liquid nitrogen and processed for histological evaluation of the chondral surface. Light and scanning electron microscopy, and immunohistochemical evaluation of type II collagen damage will be utilized to determine if permanent damage is present after sampling. If so, the tip of the fiber optic can be modified to minimize stress points.

It will be appreciated that the instant specification is set forth by way of illustration and not limitation, and that various modifications and changes may be made without departing from the spirit and scope of the present invention.

What is claimed is:

1. A method for the evaluation of the ultrastructure of connective tissue comprising:
    (a) providing a fiber optic probe operative in the mid-infrared or near-infrared region of the electromagnetic spectrum,
    (b) positioning the probe to be in contact with the surface of the connective tissue for detecting attenuated total reflectance or within a sufficient distance from the surface of the connective tissue for detecting reflection, (c) detecting mid-infrared radiation or near-infrared radiation penetrating the surface of the connective tissue for detecting attenuated total reflectance or reflecting off of the surface of the connective tissue for detecting reflection, and (d) analyzing said infrared radiation from step (c) for at least one of peak height, peak area and frequency and comparing at least one of the peak height, the peak area and the frequency to established values for at least one of peak height, peak area and frequency for normal connective tissues to detect a modification in the molecular structure of the connective tissue, and determining the progression of degradation or repair of the connective tissue, said connective tissue being selected from the group consisting of cartilage, ligament, tendon, capsule and bone.

2. The method of claim 1, wherein the probe detects said infrared radiation by attenuated total reflectance.

3. The method of claim 2, wherein the analyzing step (d) is carried out by peak frequency shift analysis.

4. The method of claim 2, wherein the analyzing step (d) is carried out by peak area analysis.

5. The method of claim 2, wherein the analyzing step (d) is carried out by a combination of peak frequency shift analysis and peak area analysis.

6. The method of claim 1, wherein the connective tissue is selected from the group consisting of articular cartilage and meniscal cartilage.

7. The method of claim 1, wherein the connective tissue is a soft connective tissue.

8. The method of claim 1, wherein the connective tissue is cartilage.

9. The method of claim 1, wherein the evaluation of the ultrastructure of the connective tissue is carried out in vivo.

10. The method of claim 1, wherein the evaluation of the ultrastructure of the connective tissue is carried out in vitro.

11. The method of claim 1, wherein the probe comprises an attenuated total reflectance element through which infrared radiation is transmitted and received.

12. The method of claim 11, wherein the analyzing step (d) is carried out by peak frequency shift analysis.

13. The method of claim 11, wherein the analyzing step (d) is carried out by peak area analysis.

14. The method of claim 11, wherein the analyzing step (d) is carried out by a combination of peak frequency shift analysis and peak area analysis.

15. The method of claim 1, wherein the probe detects infrared radiation by reflection.

16. The method of claim 15, wherein the analyzing step (d) is carried out by peak frequency shift analysis.

17. The method of claim 15, wherein the analyzing step (d) is carried out by peak area analysis.

18. The method of claim 15, wherein the analyzing step (d) is carried out by a combination of peak frequency shift analysis and peak area analysis.

19. The method of claim 1, wherein the infrared radiation is near-infrared radiation.

20. The method of claim 1, wherein the infrared radiation is mid-infrared radiation.

* * * * *